(12) United States Patent
Lewis et al.

(10) Patent No.: US 7,365,220 B2
(45) Date of Patent: Apr. 29, 2008

(54) PROCESS FOR THE RECOVERY OF ALKOXYSILANES OBTAINED FROM THE DIRECT REACTION OF SILICON WITH ALKANOLS

(75) Inventors: Kenrick Martin Lewis, Flushing, NY (US); Hua Wang, Clifton Park, NY (US)

(73) Assignee: Momentive Performance Materials Inc., Wilton, CT (US)

( * ) Notice: Subject to any disclaimer, the term of this patent is extended or adjusted under 35 U.S.C. 154(b) by 227 days.

(21) Appl. No.: 11/238,199

(22) Filed: Sep. 29, 2005

(65) Prior Publication Data

US 2007/0073076 A1    Mar. 29, 2007

(51) Int. Cl.
*C07F 7/04* (2006.01)
(52) U.S. Cl. ...................................... 556/482
(58) Field of Classification Search ............ None
See application file for complete search history.

(56) References Cited

U.S. PATENT DOCUMENTS

| | | |
|---|---|---|
| 4,727,173 A | 2/1988 | Mendicino |
| 4,761,492 A | 8/1988 | Childress et al. |
| 4,778,910 A | 10/1988 | Stoffer et al. |
| 4,941,893 A | 7/1990 | Hsieh et al. |
| 4,999,446 A | 3/1991 | Moody et al. |
| 5,503,657 A * | 4/1996 | Bouard et al. ............... 95/45 |
| 5,728,858 A | 3/1998 | Lewis et al. |
| 6,255,514 B1 | 7/2001 | Brand et al. |
| 6,861,546 B1 | 3/2005 | Ferguson |

FOREIGN PATENT DOCUMENTS

| | | |
|---|---|---|
| JP | 60/252488 | 12/1985 |
| JP | 61/039955 | 5/1994 |
| WO | WO 02/070112 | 9/2002 |

* cited by examiner

*Primary Examiner*—Samuel A Barts
(74) *Attorney, Agent, or Firm*—Dominick G. Vicari

(57) ABSTRACT

A process is provided for separating a mixture of alkoxysilanes and alkanol, e.g., the crude product effluent of the Direct Reaction of silicon metal with alkanol, which comprises:

a) introducing a mixture of alkoxysilane(s) and alkanol to a separation unit possessing a separation membrane having a first surface and an opposing second surface;

b) contacting the mixture of alkoxysilane(s) and alkanol with the first surface of the separation membrane whereby one or more components of the mixture selectively absorb into the first surface and permeate therethrough to the second surface under the influence of a concentration gradient across the membrane thereby separating the mixture into an alkanol-enriched permeate fraction and an alkanol-deficient retentate fraction or an alkoxysilane-enriched permeate fraction and an alkoxysilane-deficient retentate fraction; and, c) recovering the permeate fraction.

16 Claims, 2 Drawing Sheets

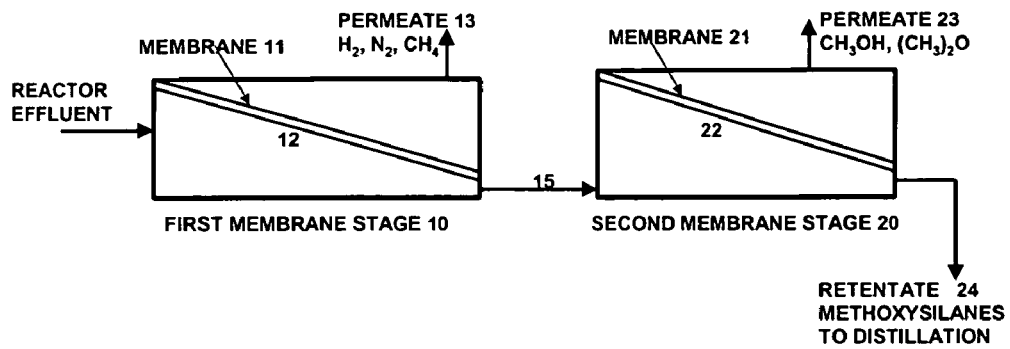
FIGURE 1A: SCHEMATIC OF TWO-STAGE MEMBRANE SEPARATION PROCESS
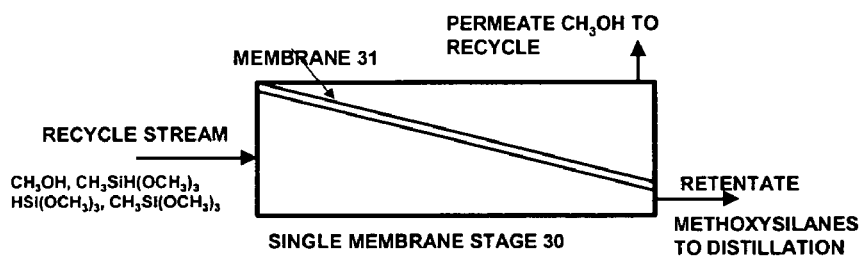
FIGURE 1B: SCHEMATIC OF SINGLE STAGE MEMBRANE SEPARATION PROCESS

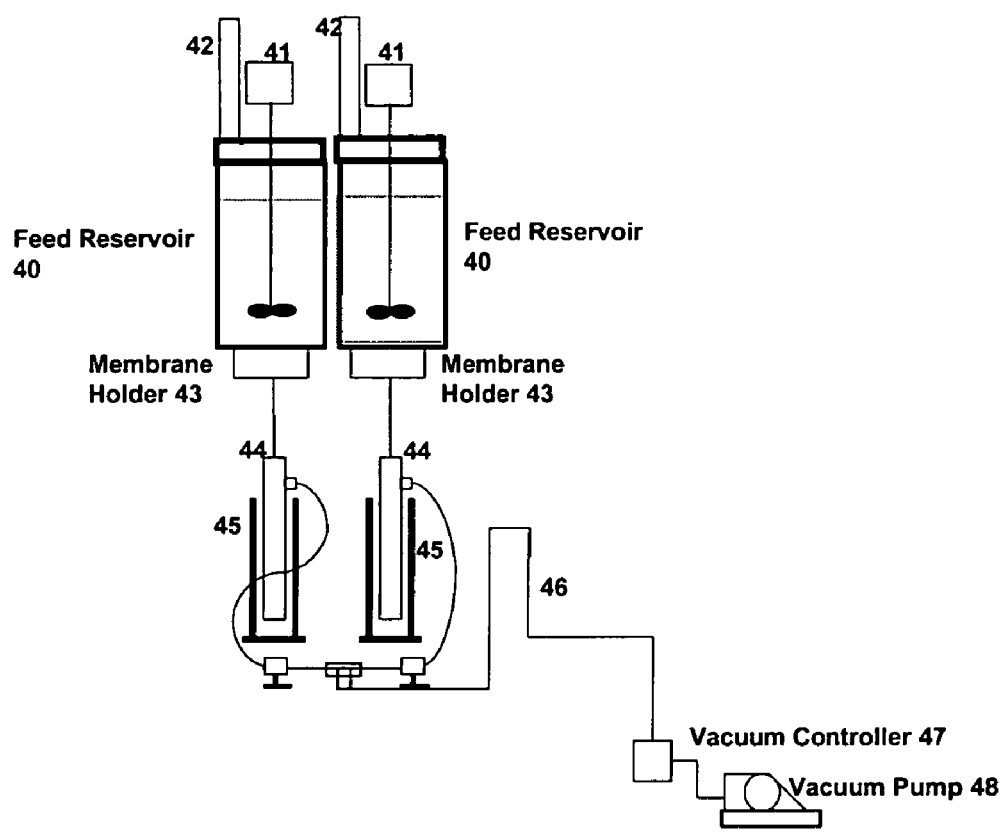
FIGURE 2: SCHEMATIC OF LABORATORY PERVAPORATION APPARATUS

PROCESS FOR THE RECOVERY OF ALKOXYSILANES OBTAINED FROM THE DIRECT REACTION OF SILICON WITH ALKANOLS

BACKGROUND OF THE INVENTION

The process of the invention relates to the separation and recovery of alkoxysilanes, particularly alkyldialkoxysilanes, from crude reaction mixtures obtained from the Direct Reaction of silicon with alkanols. More particularly, this invention is directed to the membrane separation and recovery of methyldimethoxysilane ($CH_3SiH(OCH_3)_2$) from a crude reaction mixture obtained from the Direct Reaction of silicon with methanol.

The Direct Reaction Process, as it will be referred to herein, of silicon metal with an alkanol to form trialkoxysilanes has achieved commercial prominence especially where methanol is the alcohol and the product is trimethoxysilane (see, e.g., *Chemical Engineering*, November 1999, pp. 92-93). Despite the commercial success of this process, practical problems still exist, the most important of which is that the methanol/silicon reaction is incomplete and the product stream exiting the reaction zone is primarily a mixture of unreacted methanol, trimethoxysilane product and tetramethoxysilane by-product together with minor amounts of other co-products at much lower levels. A number of problems attend the processing and separation of the product stream. Firstly, unreacted methanol and trimethoxysilane product form a low-boiling azeotrope consisting of a nearly 3/1 molar ratio of methanol to trimethoxysilane. Secondly, methanol and trimethoxysilane react with each other to form tetramethoxysilane and hydrogen gas, and can do so violently if the self-accelerating decomposition temperature of the azeotrope is exceeded, or if the azeotrope contacts certain catalytic contaminants. Thirdly, one of the minor co-products, namely, methyldimethoxysilane, has utility and economic value apart from trimethoxysilane for making a variety of silane coupling agents or intermediates possessing only two methoxy groups bonded to the silicon atom. Isolation of methyldimethoxysilane is hampered not only by the aforementioned methanol/trimethoxysilane azeotrope but also by the occurrence of a methanol/methyldimethoxysilane azeotrope.

Processes have been developed to deal with these azeotropes. For example, solvents have been added to the azeotropes either to form new, even lower-boiling azeotropes or to extract product away from methanol. The former route employing hexane is disclosed in JP 61/039955 (*Chem. Abstr.*, 106, 33302 k(1987)), and the latter employing polydimethylsiloxane is disclosed in JP 60/252488 (*Chem. Abstr.*, 104, 148307s(1986)). Similarly, in U.S. Pat. No. 4,761,492, an extractive distillation using tetramethoxysilane is disclosed. These processes all involve the handling of significant quantities of solvents and are therefore undesirable from an economic viewpoint. They also lead to a less pure grade and lower yield of trimethoxysilane due to the more extensive distillations that are required for their removal.

Most of these difficulties are avoided by the process disclosed in U.S. Pat. No. 4,999,446 wherein the cited azeotropes are recycled directly to the reaction zone thereby enabling continuous partial recovery of the trimethoxysilane portion of the methanol/trimethoxysilane azeotrope while the methanol portion undergoes further reaction with silicon metal. In this mode, the possibility of undesired reaction of methanol with trimethoxysilane is no greater than that during normal operation of the reactor and is controlled by adjusting the total flow of fresh and recycled methanol to the reactor.

More recently, U.S. Pat. No. 6,255,514 discloses treatment of the methanol/trimethoxysilane azeotrope with a salt in the optional presence of a solvent. However, there is still the problem of handling significant quantities of solvent compounded by the problem of adding a solid salt. A similar method of purifying alkoxysilanes other than trimethoxysilane is disclosed in U.S. Pat. No. 6,861,546.

The ethanol/silicon Direct Reaction Process has also achieved some level of commercial success. However, ethanol-containing azeotropes have not been observed in the reactor effluent. Nevertheless, the formation of ethyldiethoxysilane, corresponding to methyldimethoxysilane in the methanol Direct Reaction Process, does occur.

Although, in current commercial practice, the respective alkyldialkoxysilanes are usually present at low levels in the crude reaction mixture (typically less than 5 weight percent), processes are known whereby the yield of alkyldialkoxysilane can be increased. For example, U.S. Pat. No. 4,778,910 describes the reaction of methanol with copper-silicon alloy in the presence of an alkali metal co-catalyst (for example, potassium formate) under autogenous conditions at about 200-400° C. to produce a methoxysilane mixture containing about 8-9 weight percent methyldimethoxysilane. Accordingly, separation and recovery of alkyldialkoxysilanes from trialkoxysilanes and tetraalkoxysilanes and unreacted alkanol in the reactor effluent of the alkanol/silicon Direct Reaction Process is both desirable and necessary, even when azeotropes are not formed.

Thus, there is a continuing need for a process which, for example, will separate a methanol/trimethoxysilane azeotrope into its components, or at least into two fractions richer in each respective component than the original azeotrope, said process being continuous in nature, optionally with recycle of either fraction to the reactor or to the distillation column, for improved separation. Such a process should keep the methyldimethoxysilane co-product with the enriched trimethoxysilane fraction such that the co-product can be further enriched (for example, by distillation) and isolated as a separate product. In addition, there is a continuing need for an alkanol/silicon Direct Reaction Process which will provide higher yields of alkyldialkoxysilanes, the isolation of which will be enhanced by the aforesaid separation process.

A membrane is a barrier, which permits one or more components of a mixture to selectively permeate it thereby changing the composition of the fluid stream traversing it. Molecular size, molecular mass and cohesive energy density (solubility parameter) are commonly the bases of separation and the driving force for the separation can be pressure, concentration or electric potential gradient. The rate of transport (permeability) of the components and the selective permeation of components are the most important functional characteristics of a membrane. These characteristics are combined quantitatively in the permselectivity property of the membrane, defined as the ratio of the permeabilities of a component and a reference (standard). Permselectivity is the most distinctive property of a membrane. Components of higher permselectivity become enriched on the permeate side of the membrane relative to their concentrations in the feed composition.

Membranes are obtained from a variety of polymeric and inorganic materials. Examples include silicones, polysulphones, polycarbonates, polytetrafluoroethylene, nylon, silica, stainless steel, palladium, silver, alumina and zirconia. Membranes can be constructed as sheets, hollow fibers, spirals and tubes to maximize surface area/volume ratio. Comprehensive descriptions of the state-of-the-art in membrane materials, configuration, classification and applications can be found in the following publications: H. K. Lonsdale, *J. Membrane Sci.,* 10(1982) pp 81-181; J. A. Howell, "The Membrane Alternative Energy Implications for Industry", *Watt Committee Report Number* 21, Elsevier Applied Science, London (1990); G. Saracco and V. Specchia, *Catalysis Reviews—Science & Engineering,* 36(1994) pp 305-384; *Catalysis Today,* 25 Nos. 3 and 4 (1995), pp. 197-291; A. Tavolaro and E. Drioli, *Advanced Materials,* 11(1999), pp. 975-996; and, M. A. Mazid and T. Matsuura, *Separation Science and Technology,* 28(1993) pp. 2287-2296.

Application of separation processes which involve the use of porous and/or dense semi-permeable membranes for separating compounds can save in process costs because energy consumption is low, raw materials and intermediates can be recovered and reused. When the feed is in liquid state, the separation processes using membrane technology include nanofiltration, reverse osmosis, pervaporation, perstraction, and electrodialysis. When the feed is in gas or vapor phase, the separation processes using membrane technology include vapor permeation and gas permeation.

Nanofiltration and reverse osmosis involve feeding a liquid mixture on one side of a membrane at high operating pressures, while maintaining the system on the opposite side of the membrane at atmospheric pressure. Thus, the resulting permeate remains in the liquid phase. Conventional nanofiltration and reverse osmosis membranes are fabricated from cellulose derivatives and interfacial polyamide thin film composites. A disadvantage of the reverse osmosis and nanofiltration process employing conventional membranes is that the highest concentration of the liquid mixture that can be obtained is about twenty percent due to the high osmotic pressure requirements.

The pervaporation process involves feeding a liquid mixture on one side of a membrane at or near atmosphere pressure, while maintaining the system on the opposite side of the membrane at a sufficiently low vapor pressure to vaporize the liquid component(s). The resulting permeate traverses the membrane as a vapor and is collected either in its gaseous state or recovered by condensation, adsorption or any other suitable method. Instead of a vacuum on the downstream side of the membrane, a sweep gas can be used to remove the permeated product. In this mode of operation, the permeate side is at atmospheric pressure. Vapor permeation differs from pervaporation in that the feed is already in the vapor phase.

The advantages of pervaporation and vapor permeation processes are that they are applicable to the separation of azeotropic mixtures that cannot be separated by an ordinary distillation, or to the separation of a mixture of compounds having close boiling points, or to the concentration of a compound which is sensitive to heat, or to the separation of isomers. Moreover, unlike reverse osmosis, these separations or concentrations are applicable over the entire concentration range that is to be treated.

In a perstraction process, the permeate molecules in the feed dissolve into the membrane film, diffuse through the film and reemerge on the permeate side under the influence of a concentration gradient. A sweep flow of liquid is used on the permeate side of the membrane to maintain the concentration gradient driving force.

Hagerbaumer et al., *AICHE Chemical Engineering Progress, Symposium Series* 10, 50(1954), pp. 25-50 disclose the use of membranes for the separation of azeotropes. However, no mention is made in this publication of the application of membrane technology to the separation and recovery of silanes and/or silicones. Additionally, membranes have found widespread utility for water/alcohol separation, air separation, hydrogen recovery and the separation and recovery of a wide range of organic compounds and drugs.

U.S. Pat. No. 4,941,893 and Hsieh et al., *J. Membrane Sci,* 70(1992) pp 143-152 both disclose the separation of monosilane ($SiH_4$) and halosilanes from hydrogen and hydrogen halides using polysulfone membranes. WO 2002/070112 discloses the use of hydrophobic pervaporation membranes (for example, a composite polyvinyledene membrane coated with silicone rubber) for the separation of cyclic siloxanes from aqueous silicone emulsions. None of these publications describing membrane separation of silicon compounds deals with the separation and recovery of alkyldialkoxy-silanes.

Alkyldialkoxysilanes such as methyldimethoxysilane and ethyldiethoxysilane are useful raw materials for the hydrosilylation of unsaturated substrates to prepare organofunctional silanes used in coatings and surface modification. Examples of these organofunctional silanes are methylvinyldimethoxysilane, gamma-aminopropylmethyl-dimethoxysilane and glycidoxypropylethyldiethoxysilane. Methyldimethoxysilane and ethyldiethoxysilane are also desirable as starting materials for plasma-enhanced chemical vapor deposition of low dielectric constant silicate coatings on silicon wafers.

BRIEF DESCRIPTION OF THE INVENTION

It is an object of the invention to provide a process for the separation of alkoxysilane from its admixture with alkanol employing a permselective membrane.

It is a specific object of the invention herein to provide a membrane separation method for the recovery of alkyldialkoxysilanes from the crude product mixture resulting from the Direct Synthesis Process for making trialkoxysilanes, in particular, the recovery of methyldimethoxysilane from a crude trimethoxysilane reaction product.

It is yet another object of the invention to effect such recovery while obviating or minimizing the alcoholysis of SiH bonds and/or the disproportionation of the trialkoxysilanes.

By way of achieving these and other objects of the invention, there is provided a process for separating a mixture of alkoxysilanes and alkanol which comprises:

a) introducing a mixture of alkoxysilane(s) and alkanol to a separation unit possessing a separation membrane having a first surface and an opposing second surface;

b) contacting the mixture of alkoxysilane(s) and alkanol with the first surface of the separation membrane whereby one or more components of the mixture selectively absorb into the first surface and permeate therethrough to the second surface under the influence of a concentration gradient across the membrane thereby separating the mixture into an alkanol-enriched permeate fraction and an alkanol-deficient retentate fraction or an alkoxysilane-enriched permeate fraction and an alkoxysilane-deficient retentate fraction; and, c) recovering the permeate fraction.

The foregoing process is especially advantageously employed for the recovery of alkyldialkoxysilanes present in the crude product mixtures obtained from the Direct Reaction Process for making alkoxysilanes.

DESCRIPTION OF THE DRAWINGS

FIG. 1A is a schematic representation of a two-stage membrane separation process in accordance with the invention for treatment of an entire product effluent from the Direct Reaction Process for making methoxysilanes and the recovery of methyldimethoxysilane from the <66° C. normal boiling point fraction;

FIG. 1B is a schematic representation of a single stage membrane separation process in accordance with the invention for the recovery of methyldimethoxysilane from the <66° C. normal boiling point fraction of the recycle stream from the Direct Reaction Process for making methoxysilanes; and, FIG. 2 is a schematic representation of a laboratory-scale pervaporation apparatus that can be used to carry out the process of this invention.

DETAILED DESCRIPTION OF THE INVENTION

Table 1 lists the components of a typical gaseous effluent from the Direct Reaction Process for making methoxysilanes. In one current practice as disclosed in U.S. Pat. No. 4,999,446, the reaction effluent is introduced into a stripper column for the separation and recycle of components boiling <66° C. Owing to the closeness of the boiling points of the methoxysilane compounds and the occurrence of azeotropes, the recovery of methyldimethoxysilane by distillation is not practical. Methydimethoxysilane is converted to methyltrimethoxysilane when it is recycled to the reactor. All of the product recovery-complicating azeotropes contain methanol. Accordingly, the instant invention postpones distillation of the individual methoxysilanes until methanol has been substantially removed from the reaction mixture.

TABLE 1

Components of Typical Effluent of the Direct Reaction Process for Making Methoxysilanes

| COMPONENT | BOILING POINT, ° C. |
|---|---|
| $H_2$ | −252.87 |
| $N_2$ | −195.8 |
| $CH_4$ | −164 |
| $(CH_3)_2O$ | −23 |
| $CH_3OH$ | 64.5 |
| $CH_3SiH(OCH_3)_2$ | 61 |
| Azeotrope 1: 23.1 wt % $CH_3OH$/76.9 wt % $CH_3SiH(OCH_3)_2$ | 54 |
| Azeotrope 2: 45 wt % $CH_3OH$/55 wt % $HSi(OCH_3)_3$ | 62.5 |
| Azeotrope 3: 85 wt % $CH_3OH$/15 wt % $CH_3Si(OCH_3)_3$ | 65 |
| $HSi(OCH_3)_3$ | 84 |
| $CH_3Si(OCH_3)_3$ | 102 |
| $Si(OCH_3)_4$ | 122 |
| Condensed Silicates | 150-250 |
| Therminol® 59 | 280-330 |

Where alkoxysilane-alcohol azeotropes are not known to exist, as in the product mixture from the Direct Synthesis Process for making ethoxysilanes, membrane separation can effect the safe removal of ethanol from the crude product while minimizing conversion of trialkoxysilane to tetraalkoxysilane. The SiH alcoholysis reaction can be quite pronounced during temporary storage, stripping and distillation. Hydrogen generation from this exothermic reaction also presents a potential hazard. Thus, ethanol separation through a suitable membrane in accordance with the process of this invention can prevent or minimize loss of the trialkoxysilane as well as contribute to safe operation.

Membrane separation can also be employed to separate alkoxysilane-alkanol mixtures in which the alkoxysilanes do not contain functional groups that are reactive with the alkanol. Alkyltrialkoxysilane-alkanol mixtures and tetraalkoxysilane-alkanol mixtures are representative examples. The mixture to be separated can be fed to the retentate side of the membrane as a liquid or a vapor. A pressure gradient for preferential transport is generated on the permeate side of the membrane. When the pressure gradient is effected by vacuum or by the flow of an inert sweep gas, the membrane separation is referred to as pervaporation. The components of the mixture that diffuse through the membrane are vaporized by the reduced pressure. They are removed from the permeate side of the membrane and recovered by condensation, adsorption or any other suitable method. The separation of mixtures of tetramethoxysilane and methanol by pervaporation is illustrated hereinunder in the examples presented below.

In one embodiment of the present invention, the process is carried out on a process stream constituting the entire crude product from the methanol—silicon Direct Reaction Process (the two stage membrane separation process of FIG. 1A). Alternatively, in another embodiment, an overhead stream with a normal boiling point of less than about 66° C. can be processed in accordance with the present invention (the single stage membrane separation process of FIG. 1). Both of these schemes are examples of vapor permeation, i.e., pervaporation in which the mixture to be separated is fed as a vapor to the upstream side of the membrane.

M. Asaeda et al. (J. Chem. Engng. Jap., 19(1986), pp. 72-77) identifies Knudsen diffusion, Poiseuille (capillary) flow, surface diffusion and molecular sieving as the four mechanisms by which gases or vapors permeate through membranes. Molecular sieving is effective in membranes with pore sizes less than 10 Angstroms (1 nanometer). Knudsen diffusion dominates when the mean free path is greater than ten times the pore diameter. Under Knudsen diffusion, separation efficiency between methanol and the methoxysilanes is determined by the square root of the ratio of molecular weights. This value is 1.82 for methanol/methyldimethoxysilane, 1.95 for methanol/trimethoxysilane and 2.06 for methanol/trimethoxysilane.

Table 2 below sets forth the molecular weight (daltons), molar volume ($10^3$ $m^3$/kg mole and molecular diameters (nm)) of the individual components of the gaseous and liquid components of the crude product streams obtained from the Direct Reaction Process for making methoxysilanes and ethoxysilanes.

TABLE 2

Molecular Weight, Molar Volumes and Molecular Diameters of the Components of Crude Product Streams Obtained From the Direct Reaction Process

| Component | Molecular Weight, daltons | Molar Volume, $10^3$ $m^3$/kg mole | Molecular Diameter, nm |
|---|---|---|---|
| $H_2$ | 2.016 | 26.199 | 4.36[a] |
| $N_2$ | 28.014 | 33.989 | 4.76[a] |
| $CH_4$ | 16.04 | 37.97 | 4.90[a] |
| $(CH_3)_2O$ | 46.07 | 62.707 | 5.85[a] |
| $CH_3OH$ | 32.04 | 42.90 | 5.14[b] |
| $CH_3SiH(OCH_3)_2$ | 106.20 | 137.24 | 7.58[b] |
| $HSi(OCH_3)_3$ | 122.13 | 145.36 | 7.72[b] |
| $CH_3Si(OCH_3)_3$ | 136.22 | 169.09 | 8.12[b] |

TABLE 2-continued

Molecular Weight, Molar Volumes and Molecular Diameters of the Components of Crude Product Streams Obtained From the Direct Reaction Process

| Component | Molecular Weight, daltons | Molar Volume, $10^3$ m$^3$/kg mole | Molecular Diameter, nm |
|---|---|---|---|
| Si(OCH$_3$)$_4$ | 152.22 | 177.21 | 8.25[b] |
| C$_2$H$_5$OH | 46.07 | 60.91 | 5.78[a] |
| C$_2$H$_5$SiH(OC$_2$H$_5$)$_2$ | 148.21 | 204.58 | 8.66[b] |
| HSi(OC$_2$H$_5$)$_3$ | 164.28 | 214.32 | 8.79[b] |
| C$_2$H$_5$Si(OC$_2$H$_5$)$_3$ | 192.33 | 257.07 | 9.34[b] |
| Si(OC$_2$H$_5$)$_4$ | 208.33 | 266.81 | 9.46[b] |

[a]These values were calculated from critical properties according to R. C. Reid and T. K. Sherwood, "The Properties of Gases and Liquids", McGraw-Hill, N.Y., 1958, p. 52.
[b]These values were calculated according to W. Schotte, Chem. Engng. J., 48(1992), pp. 167-172.

In a first embodiment of the process of the invention schematically illustrated in FIG. 1A, gaseous components (hydrogen, nitrogen and methane) of a crude product effluent from a Direct Reaction Process for making methoxysilanes are separated by contact with the first (feed) side 12 of a first permselective membrane 11 in a first membrane separation stage 10 to provide a first gaseous permeate on opposing second (permeate) side 13 of the membrane and a first retentate 15 comprising the methoxysilane components of the initial product effluent stream, primarily methyldimethoxysilane and trimethoxysilane, of much-reduced gaseous content. Hydrogen recovered from first gaseous permeate 13 can be used for any suitable application, e.g., in other chemical processes, fuel cell operations, etc. First retentate 15 is then introduced into a second membrane separation stage 20 where it is contacted with the retentate side 22 of a second permselective membrane 21 to provide a second permeate 23 made up of components of relatively small molecular diameter (methanol and dimethyl ether) and a second retentate 24 of much-enriched methoxysilane content.

Second membrane stage 20 effects the breaking of the three methanol/methoxysilane azeotropes identified in Table 1, supra, leaving a storage-stable mixture of methoxysilanes and higher boilers which can thereafter be separated into its individual silane components, i.e., methyldimethoxysilane, trimethoxysilane, methyltrimethoxysilane and tetramethoxysilane, by fractional distillation. The approximately 20° C. difference in normal boiling points between the silanes in second retentate 24 and the substantial absence of azeotropes therein greatly facilitates the fractional distillation operation. Methanol recovered from second permeate 23 can, if desired, be recycled to the Direct Reaction Process for reaction with silicon to produce methoxysilane product.

Membrane separation stages 10 and 20 include one or more membrane elements connected to one or more vacuum pumps or compressors, which, in operation, provide a concentration and pressure gradient to provide a flow of permeating components of the feed through the individual membranes. The individual membranes can be configured as sheets, spirals, fibers, honeycombs or other effective configuration. Crude alkoxysilane feed flow into or across the membranes can be either on the shell side or through the lumen. The permeating gases are drawn through to the opposite side. Multiple membranes can be combined in series or in parallel to obtain the desired degree of separation. When arranged in series, the output of an anterior membrane (or assembly of membranes) becomes the feed for the next membrane downstream, and so on, until a desired level of separation efficiency is achieved.

Depending on the composition of a particular crude feed, its temperature, the characteristics of the permselective membrane(s), the nature of both the permeate and the retentate desired and other factors familiar to those skilled in the art, the pressure gradient across the membranes can be made to vary over fairly wide limits. For example, the vacuum level on the downstream side of the pervaporation membrane can be below 400 torr, advantageously below 100 torr, and more advantageously below 20 torr.

Since the molecular diameters of methanol, dimethyl ether and methane (see Table 2, supra) are relatively close to each other, it is possible that some dimethyl ether and methanol may be removed in first membrane separation stage 10. Thus, in another embodiment of the process of the invention (FIG. 2), a single membrane stage 30 equipped with permselective separation membrane 31 is used to separate dimethyl ether, methanol and the permeable gases from the methoxysilanes and, optionally, a second membrane stage (not shown) which is selective for methanol is employed to recover methanol from the permeate for recycle to the Direct Reaction Process. The methanol can also be recovered for recycle by condensation from the gaseous permeate. Whether a single or a two-stage membrane separation is employed, the alcohol content of the retentate alkoxysilane stream should be reduced to below about 1 weight percent, preferably below about 0.5 weight percent, to minimize or avoid the SiH alcoholysis reaction and the possibility of dangerous pressure build-up in the stored methoxysilane retentate.

Table 2, supra, also shows that methanol, ethanol and the permeable gases have molecular diameters less than about 6 nm whereas the molecular diameters of the alkoxysilanes are all greater than about 7 nm. Thus, another embodiment of the instant invention utilizes membranes, which can effect separation into these two molecular size categories.

In still another embodiment, membrane separation is applied only to the gaseous recycle stream comprising compounds and azeotropes with normal boiling points less than about 66° C. Permeate methanol is recycled to the reactor and the methoxysilanes are sent to fractional distillation. Any of these embodiments can be adapted for installation in existing commercial equipment.

As shown in the schematic illustration of a pervaporation apparatus of FIG. 2, temperature-controlled reservoirs 40 contain an alkoxysilane-alkane mixture to be separated. The mixture is kept agitated by mechanical stirrers 41. Reflux condensers 42 condense and return vapors to reservoir 40. Separation membrane holders 43 are secured to reservoirs 40 and to permeate collectors 44 which are cooled in liquid nitrogen dewars 45. A common vacuum line 46 exhausts both separation membrane holders 43. A vacuum pump 48 and associated controller 47 completes the apparatus. The reservoirs can be filled with the same or different alkoxysilane-alkanol mixtures. Similarly, the separation membranes in the two separation membrane holders can be the same or different.

A wide variety of organic, ceramic and inorganic materials can be utilized for the fabrication of the permselective membrane(s) employed in the process of the invention. With dense membranes which operate on a solution—diffusion mechanism, more selective separation is achieved when one permeating component is more soluble and has higher diffusivity in the membrane material than the others. The permeation rate is proportional to this solubility and to the diffusivity of the component through the membrane. This separation mechanism is facilitated by a good match between the solubility parameter of the polymer and that of the permeating component.

Selectivity and flux are two important parameters in the operation of a membrane separation process. They are defined as follows:

a) Selectivity=(ratio of components in permeate)/ (ratio of components in feed)

b) Flux=(total material flow through membrane)/ (membrane area×time)

In addition to having effective permselectivity for alkanol and the permeable gases relative to the product alkoxysilanes and an acceptable flux for an economically viable process, the separation membranes should also be thermally stable and unreactive with the alkoxysilanes and/or hydridosilanes at temperatures of up to about 100° C., preferably up to 200° C. and more preferably up to about 300° C. The separation membranes must also be resistant to fouling and dimensional deformation from any solvent and higher boilers (oligomeric organosilicates) that may be present at these operating temperatures. Among the organic materials, polytetrafluoroethylene and crosslinked polyamides are especially advantageous. Embodiments of inorganic materials that are useful for fabrication of the permselective membranes herein are palladium and its alloys with silver or silicon and alumina being especially advantageous. If desired, the permselective membranes can be supported on organic polymers, glass, quartz, sintered steel, etc. Table 3 below lists several organic, ceramic and inorganic materials from which permselective separation membranes useful for carrying out the process of the invention can be fabricated.

TABLE 3

Materials Suitable for Fabricating Permselective Separation Membranes

| ORGANIC POLYMERIC MEMBRANES | METALLIC, INORGANIC AND CERAMIC MEMBRANES |
|---|---|
| Polyamide | Palladium |
| Polyethylene | Palladium-silver alloy |
| Polyacrylonitrile | Palladium - silicon alloy |
| Polyphenylene oxide | Amorphous $Pd_xSi_{(1-x)}$, x = 0.8-0.9 |
| Polysulfone | Silica |
| Polypropylene | Alumina |
| Silicone Rubber | Zeolite |
| Silicone-polycarbonate | Titania |
| Polytetrafluoroethylene | Pyrolytic Carbon |
| Polyvinyledene fluoride | |
| Nafion (in its H+ and alkali metal - exchanged forms) | |
| Polyimide | |
| Polyphosphazene | |

The following examples are illustrative of the membrane separation process of the invention.

ABBREVIATIONS USED

| g | Gram | PDMS | Poly(dimethyl)siloxane |
| kg | Kilogram | gc | Gas Chromatography |
| m | Meter | nmr | Nuclear magnetic resonance |
| Pa | Pascal | | |
| cm | Centimeter | mm | Millimeter |

EXAMPLE 1

This example illustrates the permselective membrane separation of a mixture of methanol and methoxysilanes obtained from the Direct Reaction Process as disclosed in U.S. Pat. Nos. 4,727,173 and 5,728,858, the entire contents of which are incorporated by reference herein.

The Direct Reaction Process for making trimethoxysilane is carried out as described in U.S. Pat. No. 4,727,173. The composition of the resulting crude reaction mixture, the membrane input and the permeate and retentate fractions are set forth in Table 4 as follows:

TABLE 4

Compositions (Wt %) of the Crude Feed, the Membrane Input and Separated Fractions

| Component | Crude Composition | Membrane Input | Permeate Fraction | Retentate Fraction |
|---|---|---|---|---|
| $CH_3OH$ | 6.64 | 43.45 | 100 | 0.25 |
| $CH_3SiH(OCH_3)_2$ | 2.73 | 18.00 | | 31.44 |
| $HSi(OCH_3)_3$ | 84.14 | 37.30 | | 66.15 |
| $CH_3Si(OCH_3)_3$ | 0.18 | 1.25 | | 2.16 |
| $Si(OCH_3)_4$ | 3.85 | | | |
| Condensed Methyl Silicates | 2.46 | | | |

To carry out the membrane separation operation, the crude product stream resulting from the Direct Reaction Process of U.S. Pat. No. 4,727,173 is introduced to the middle of the distillation column assembly of U.S. Pat. No. 5,728,858. Temperature at the top of the distillation column varies between 55-66° C. Stainless steel tubing connecting the azeotrope recycle line of the distillation column to the membrane separator is heated and valved to allow operation with and without the membrane separator.

Membrane separation is achieved with a Membralox® porous alumina tube sealed gas-tight in a 55 cm long by 2.54 cm outer diameter stainless steel shell and maintained at 70-100° C. with external wall heating. The Membralox® alumina tube is 50 cm long by 0.635 centimeter internal diameter. The stainless steel shell has an outlet for the withdrawal of methanol permeate. The feed consisting of methanol and methoxysilanes (membrane input composition in Table 4) is introduced to the lumen of the alumina tube via stainless steel tubing. Vacuum is applied at the outlet of the stainless steel shell to aid the permeation. The pressure on the permeate side of the membrane varies between 933-6666 Pa (7-37.5 mm Hg). Retentate is primarily a mixture of methoxysilanes, which is condensed after exiting the membrane tube. This mixture is thereafter fractionally distilled to obtain separate methyldimethoxysilane and trimethoxysilane fractions.

EXAMPLE 2

This example illustrates pervaporation of the mixture of methanol and methoxysilanes produced by the Direct Synthesis processes of U.S. Pat. Nos. 4,727,173 and 5,728,858 employing the laboratory-scale pervaporation apparatus schematically illustrated in FIG. 2.

The mixture to be separated boils at 54-60° C. and has the composition: 22.20 wt $CH_3OH$, 3.28 wt % $H_2Si(OCH_3)_2$, 33.80 $CH_3SiH(OCH_3)_2$, 34.28 wt % $HSi(OCH_3)_3$, 0.65 wt % $CH_3Si(OCH_3)_3$ and 5.79 wt % $Si(OCH_3)_4$. The polyamide separation membrane was made by interfacial synthesis using piperazine, isophthaloyl chloride and trimesoyl chloride over NOMEX® ultrafiltration supports. The separation membrane is 50-200 nm thick. Separation was conducted at 60° C. with a permeate side vacuum of 1.95 mm Hg (260 Pa). Separation was substantially complete after about 100 minutes. The permeate was 99 wt % methanol as determined by gas chromatographic analysis. The retentate contained 0.26 wt % $CH_3OH$, 3.50 wt % $H_2Si(OCH_3)_2$, 44.03 wt % $HSi(OCH_3)_3$, 0.83 wt $CH_3Si(OCH_3)_3$ and 7.42 wt % $Si(OCH_3)_4$. The average flux was about 300 kg per square meter per day. The retentate was distilled fractionally for recovery of methyldimethoxysilane.

EXAMPLES 3-5

Examples 3-5 illustrate the pervaporation separation of mixtures of methanol and tetramethoxysilane employing the apparatus of FIG. 2. The membrane and separation conditions were those described in Example 2. Table 5 summarizes the results for mixtures containing approximately 30-45 weight percent methanol.

TABLE 5

Pervaporation of Methanol - Tetramethoxysilane Mixtures

| Example | FEED $CH_3OH/Si(OCH_3)_4$ | Time, min | Permeate % $CH_3OH$ | Flux, $kg/m^2/day$ | Selectivity |
|---|---|---|---|---|---|
| 3 | 37/63 | 22 | 89.65 | 324.3 | 14.74 |
| 4 | 43/57 | 60-100 | 91.56 | 295-493 | 14.39 |
| 5 | 32/68 | 100-120 | 88.53 | 300-366 | 16.40 |

The polyamide membrane afforded selective permeation of methanol from its mixtures with tetramethoxysilane. The retentate in the reservoir was enriched in tetramethoxysilane.

EXAMPLE 6

This example illustrates the separation of methanol/tetramethoxysilane mixtures whereby methanol is the retentate and tetramethoxysilane is the permeate.

A PDMS membrane was used in the pervaporation apparatus illustrated in FIG. 2. The mixture to be separated contained 43 wt % $CH_3OH$ and 57 wt % $Si(OCH_3)_4$. Vacuum, 67-267 Pa (0.5-2 mm Hg) was applied to the permeate side. NMR analysis of the permeate showed 4.5 wt % methanol and 94.5 wt % $Si(OCH_3)_4$. Selectivity was 16 and flux 150 $kg/m^2/day$.

While the process of the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the process of the invention but that the invention will include all embodiments falling within the scope of the appended claims.

What is claimed is:

1. A process for separating the components in a process stream resulting from the Direct Reaction Process of silicon metal with an alkanol for making alkoxysilanes, which comprises:

a) introducing the process stream from the Direct Reaction Process to a separation unit possessing a separation membrane having a first surface and an opposing second surface, wherein the process stream includes a mixture of alkoxysilane(s), alkanol(s) and optionally alkanol/alkoxysilane azeotropes;

b) contacting the process stream from the Direct Reaction Process with the first surface of the separation membrane whereby one or more components of the mixture of alkoxysilane(s), alkanol(s) and optionally alkanol/alkoxysilane azeotropes selectively absorb into the first surface and permeate therethrough to the second surface under the influence of a concentration gradient across the membrane thereby separating the mixture into an alkanol-enriched permeate fraction and an alkanol-deficient retentate fraction or an alkoxysilane-enriched permeate fraction and an alkoxysilane-deficient retentate fraction; and, c) recovering the permeate fraction and the retention fraction.

2. The process of claim 1 wherein the process stream from the Direct Reaction Process comprises a mixture of methoxysilanes, methanol and methanol/methoxysilane azeotropes, the process resulting in the breaking of the azeotropes.

3. The process of claim 2 wherein the methoxysilanes in the retentate fraction are separated by fractional distillation.

4. The process of claim 2 wherein recovered methanol is recycled to the Direct Reaction Process.

5. The process of claim 1 wherein the concentration gradient is maintained by vacuum applied to the second surface.

6. The process of claim 1 wherein the concentration gradient is maintained by the application of pressure to the first surface that is higher than the pressure on the second surface.

7. The process of claim 2 conducted in two membrane separation stages, the process stream additionally containing hydrogen, nitrogen and methane gases undergoing a first membrane separation step in a first membrane separation zone equipped with a first separation membrane to provide a first permeate fraction comprising hydrogen, nitrogen and methane and a first retentate fraction of substantially reduced gas content comprising methoxysilanes, methanol and methanol/methoxysilane azeotropes, the first retentate fraction undergoing a second membrane separation step in a second membrane separation zone equipped with a second separation membrane to provide a second permeate fraction comprising methanol and a second retentate fraction possessing a higher concentration of methoxysilanes than that present in the first retentate fraction, the second membrane separation step resulting in the breaking of the azeotropes.

8. The process of claim 7 wherein methanol recovered in the second permeate fraction is recycled to the Direct Reaction Process.

9. The process of claim 7 wherein methoxysilanes present in the second retentate fraction are separated by fractional distillation.

10. The process of claim 1 wherein the process stream is obtained from the Direct Reaction Process and comprises a mixture of ethoxysilanes and ethanol.

11. The process of claim 10 wherein the ethoxysilanes in the retentate fraction are separated by fractional distillation.

12. The process of claim 10 wherein the ethanol recovered in the permeate fraction is recycled to the Direct Reaction Process.

13. The process of claim 1 wherein the separation membrane is fabricated from at least one material selected from the group consisting of polyamide, palladium, polyethylene, palladium-silver alloy, polyacrylonitrile, palladium-silicon alloy, polyphenylene oxide, amorphous $Pd_xSi_{(1-x)}$, x=0.8-0.9, polysulfone, silica, polypropylene, alumina, silicone rubber, zeolite, silicone-polycarbonate, titania and polytetrafluoroethylene, pyrolytic carbon, polyvinyledene fluoride, nafion(in its H+ and alkali metal—exchanged forms) and polyphosphazene, the separation membrane being optionally supported by another material.

14. The process of claim 7 wherein the first and second separation membranes are fabricated from different materials selected from the group consisting of polyamide, palladium, polyethylene, palladium-silver alloy, polyacrylonitrile, palladium-silicon alloy, polyphenylene oxide, amorphous $Pd_xSi_{(1-x)}$, x=0.8-0.9, polysulfone, silica, polypropylene, alumina, silicone rubber, zeolite, silicone-polycarbonate, titania and polytetrafluoroethylene, pyrolytic carbon, polyvinyledene fluoride, nafion (in its H+ and alkali metal—exchanged forms) and polyphosphazene, one or both separation membranes being optionally supported by another material.

15. The process of claim 1 wherein the alkoxysilane includes a trialkoxysilane.

16. The process of claim 15 wherein the trialkoxysilane is trimethoxysilane.

* * * * *